(12) United States Patent
Andersen et al.

(10) Patent No.: US 11,248,094 B2
(45) Date of Patent: Feb. 15, 2022

(54) CROSSLINKING OF BIOPOLYMERS IN A SEMI-SOLID STATE

(71) Applicant: SolyPlus GmbH, Haselund (DE)

(72) Inventors: Richard Dolph Andersen, Berlin (DE); Annette Assogba-Zandt, Berlin (DE); Elena Maltseva, Schöneiche (DE); Andreas Voigt, Berlin (DE)

(73) Assignee: SOLYPLUS GMBH, Haselund (DE)

( * ) Notice: Subject to any disclaimer, the term of this patent is extended or adjusted under 35 U.S.C. 154(b) by 2 days.

(21) Appl. No.: 16/753,500

(22) PCT Filed: Oct. 9, 2018

(86) PCT No.: PCT/IB2018/057791
§ 371 (c)(1),
(2) Date: Apr. 3, 2020

(87) PCT Pub. No.: WO2019/073364
PCT Pub. Date: Apr. 18, 2019

(65) Prior Publication Data
US 2020/0291195 A1  Sep. 17, 2020

(30) Foreign Application Priority Data

Oct. 12, 2017  (DE) .................. 10 2017 009 768.2

(51) Int. Cl.
| | |
|---|---|
| C08J 3/24 | (2006.01) |
| A61L 27/20 | (2006.01) |
| A61L 27/26 | (2006.01) |
| A61L 27/52 | (2006.01) |
| A61L 27/54 | (2006.01) |
| C08B 37/08 | (2006.01) |
| A61K 9/06 | (2006.01) |
| A61K 47/36 | (2006.01) |

(52) U.S. Cl.
CPC .................. *C08J 3/24* (2013.01); *A61K 9/06* (2013.01); *A61K 47/36* (2013.01); *A61L 27/20* (2013.01); *A61L 27/26* (2013.01); *A61L 27/52* (2013.01); *A61L 27/54* (2013.01); *C08B 37/003* (2013.01); *C08B 37/0072* (2013.01); *C08J 2305/08* (2013.01)

(58) Field of Classification Search
CPC ................................................. C08J 3/24–246
See application file for complete search history.

(56) References Cited

U.S. PATENT DOCUMENTS

2007/0053987 A1*  3/2007  Bayer ................ C08B 37/0081
                                                      424/488

FOREIGN PATENT DOCUMENTS

| CN | 106279728 | * | 1/2017 | |
| CN | 106496601 | * | 3/2017 | |
| WO | 2005/054440 A2 | | 6/2005 | |
| WO | 2014/206500 A1 | | 12/2014 | |
| WO | 2015/048774 A2 | | 4/2015 | |
| WO | WO-2016057603 A1 | * | 4/2016 | ............. A61L 27/52 |

OTHER PUBLICATIONS

Collins, M. et al "Physical properties of crosslinked hyaluronic . . . " J. Mater. Sci.: Mater. Med., vol. 19, pp. 3335-3343. (Year: 2008).*
EPO machine translation of CN 106279728, (Year: 2017).*
EPO machine translation of CN 106496601 (Year: 2017).*
Yoshii, F. "Application of functional polymers . . . " JAERI-Conf, 2005-005 (Proceedings of the FNCA 2004 Workshop on Application of Electron Accelerator), pp. 25-30. (Year: 2005).*
European Examination Report dated Jul. 16, 2021, in connection with corresponding EP Application No. 18 796 117.2; 7 pages.

* cited by examiner

*Primary Examiner* — Leigh C Maier
(74) *Attorney, Agent, or Firm* — Maier & Maier, PLLC

(57) ABSTRACT

The present invention relates to methods of providing biocompatible/biodegradable hydrogels obtained by crosslinking of biopolymers (for example polysaccharides or proteins) in the semi-solid (modelling-clay like) state at water content below 70% by weight. The resulting materials can be applied in medicine, pharmacy and/or in cosmetics.

16 Claims, 2 Drawing Sheets providing a polymer or a plurality of polymers as a powder mixing the polymer or the plurality of polymers with a crosslinker and an aqueous solution at a water content below 70 weight % to form a semi-solid, paste–like mass moulding the semi-solid, paste–like mass to obtain a solid body mixing a biopolymer with an aqueous solution to form a semi-solid mass placing the mass into a crosslinker solution to form a crosslinked polymer matrix

CROSSLINKING OF BIOPOLYMERS IN A SEMI-SOLID STATE

PRIORITY CLAIM

This PCT International Patent Application claims priority to German priority patent application serial number 102017009768.2, filed Oct. 12, 2017, the entire contents of which are incorporated herein in its entirety.

FIELD OF THE INVENTION

The present invention relates to methods of providing biocompatible/biodegradable hydrogels obtained by cross-linking of biopolymers (for example polysaccharides or proteins) in the semi-solid (modelling-clay like) state at water content below 70% by weight. The resulting materials can be applied in medicine, pharmacy and/or in cosmetics.

BACKGROUND

Hydrogels made of natural polymers, such as polysaccharides and proteins, are especially attractive for biomedical and cosmetic applications owing to their biocompatibility and biodegradability. Besides, their production does not require oil refinery and is less harmful to nature. Various products contain polysaccharide hydrogels: scaffolds in tissue engineering wound dressings, sustained-release drug delivery systems, implants and injectable dermal fillers, etc.

The most prominent feature of hydrogels is their ability to absorb water: they can bind more water than ten (10) times of their initial weight. They are different from viscous aqueous polymer solutions by the formation of a three-dimensional network where the neighboring polymer chains are physically or chemically crosslinked. Physical crosslinking can be achieved by secondary forces within a polymeric network such as hydrogen bonds, ionic interactions, van-der-Waals forces, while the covalent crosslinking usually involves chemical reaction between polymer backbones or between polymer backbones and crosslinking agents. Moreover, both physical and chemical crosslinking may occur in the same hydrogel simultaneously.

Among others, hydrogels obtained by chemical crosslinking of hyaluronic acid derivatives are very promising and safe for biomedical and cosmetic uses. Nowadays, hyaluronic acid is produced, e.g. using biotechnology methods, from streptococci species in industrial quantities. The hyaluronic acid or more precisely sodium hyaluronan is a linear nonsulfated glycosoaminoglycan composed of repeating D-glucuronic acid and N-acetyl-D-glucosamine, linked via alternating β-(1→4) and β-(1→3) glycosidic bonds. Hyaluronic acid takes part in many physiological processes: it is involved in skin repair mechanisms, and it is an important component of articular cartilage, it plays a lubricating role in muscular connective tissue, and it is a major component of vitreous body.

Amine containing chitosan is another example of natural polysaccharides widely used in biomedical, food and chemical industries. It forms a physical hydrogel in the presence of polyphosphates or by ionic interactions with polysaccharides containing carboxylic acid groups such as alginate, carboxymethylcellulose, and hyaluronic acid. The widely utilized gelatin and calcium alginate are physically cross-linked hydrogels likewise. Alginate is a polysaccharide containing carboxylic acid group, and it is extracted from marine brown algae or it can be produced by bacteria. Calcium alginate gels have applications in medicine for drug/protein delivery, cell encapsulation, and tissue regeneration. Gelatin is an irreversibly hydrolyzed form of collagen, a structural protein in the extracellular space in various connective tissues of animal bodies. It has a broad applicability in food and pharmacy due to its ability to dissolve in hot water and to gel on cooling.

In view of the several disadvantages of conventional methods and approaches, there is a significant, long-felt and yet unmet need for improved methods of providing biocompatible/biodegradable hydrogels.

SUMMARY OF REPRESENTATIVE EMBODIMENTS OF THE INVENTION

According to certain preferred embodiments, the present invention provides processes for producing a cross-linked biopolymer. The present invention provides preferred methods and approaches for obtaining the crosslinked polymers.

According to one preferred embodiment, a polymer or a plurality of polymers is/are provided as a powder and is/are mixed with crosslinker and an aqueous solution that may or may not contain an active ingredient at water content below 70 weight %. The semi-solid, paste-like (modelling clay-like) mass is then moulded, optionally it can be micronized in order to obtain microparticles. The reaction can be carried out at ambient temperature, or at higher temperatures compared to ambient temperature, or at lower temperatures compared to ambient temperature.

The obtained solid body can be washed free from undesired components (ions, non-reacted crosslinker molecules, byproducts) in the excess amount of the aqueous solution. The crosslinked polymer matrix can be loaded with other biologically active substances, for example, proteins, peptides, vitamins, antioxidants, signaling molecules, antibiotics, conventional drugs etc. and/or cells.

According to another preferred embodiment for producing a cross-linked biopolymer, the biopolymer is mixed with aqueous solution that may or may not contain an active ingredient forming a semi-solid mass, and optionally micronized. The crosslinking is realized preferably by placing the kneaded mass (before or after drying) into a cross-linker solution.

DETAILED DESCRIPTION OF PREFERRED EMBODIMENTS OF THE INVENTION

Figure 1:
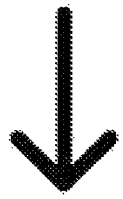
FIG. 1 depicts one preferred method of producing a cross-linked biopolymer.
Figure 1:
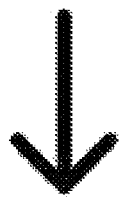

Reference will now be made in detail to various aspects of the invention and embodiments. The following language and descriptions of certain preferred embodiments of the present invention are provided to further an understanding of the principles of the present invention. However, it will be understood that no limitations of the present invention are intended, and that further alterations, modifications, and applications of the principles of the present invention are also included.

Moreover, unless otherwise defined, all numbers expressing quantities of ingredients, properties such as molecular weight, reaction conditions, and so forth used in the specification are to be understood as being modified in all instances by the term "about." Accordingly, unless indicated to the contrary, the numerical parameters set forth in the specification are approximations that may vary depending upon the desired and intended properties.

As used herein, the term "substantially" shall be understood to be a definite term that broadly refers to a degree that is, to a significant extent, close to absolute, or essentially absolute. For example, the term "substantially complete" shall be understood to be a definite term that broadly refers to a degree of completeness that is, to a significant extent, close to complete, or essentially complete. In other words, in certain embodiments, and by way of non-limiting example, the term "substantially complete" shall refer to a degree of completeness that is at least about ninety percent or more complete, or that is, to a significant extent, essentially 100 percent complete.

In a preferred embodiment of the present invention, a crosslinker, biopolymer or a mixture of biopolymers and an aqueous solution are mixed together at an aqueous content below about 70 weight percent (%). Alternatively, the biopolymer is mixed with aqueous solution without crosslinker; and the obtained semi-solid mass is then crosslinked in the bulk aqueous solution containing crosslinker. The obtained polymer matrix may or may not contain active ingredients.

In one embodiment, a possible soaking of the crosslinked matrix in the active ingredients solution is an option when a crosslinker (solid or liquid) is mechanically mixed (via milling and kneading or via extrusion) with a biopolymer.

In other embodiments, the crosslinking reaction can be carried out at ambient conditions as well as at lower or higher temperatures. It has been observed that the quality will increase if constant pressure is applied during the crosslinking reaction step.

There are cases of crosslinking biopolymers which are different to the schema above, if the biopolymers themselves are reacting/crosslinking with each other by an appropriate reaction. For example, polycation and polyanion are forming ionically crosslinked reaction products which are phenomenologically very similar to the main structures proposed here, or, physically crosslinked hydrogels, for example, gelatin are belonging to a similar group of semi-solid materials.

The term "wt. %" or "weight %" refers to a concentration by weight of a component (e.g., water, biopolymer etc.) in the entire composition. The preferred aqueous content in the semi-solid composition is between about 30 to 70 wt. %, and preferably 50 wt. %.

The term "aqueous solution", as used herein, refers to a solution in which the solvent is water and includes but is not limited to buffers with inorganic salts such as sodium or potassium phosphates, sodium, potassium or calcium chlorides, sodium or potassium acetate as well as organic and inorganic acids and bases such as sodium or potassium hydroxide, acetic acid etc.

The term "biopolymer" is intended to refer, but is not limited to polysaccharides—molecules comprising two or more monosaccharide units—such as sodium alginate (or alginic acid), sodium hyaluronate (or hyaluronic acid), chitosan acetate, pullulan, pectin, carrageenan, carboxymethylcellulose, chondroitin sulfate. The molecular weight of the biopolymers is at least 10000 Da, preferably from about 10000 to 4000000 Da and more preferably between about 20000 and 2000000 Da.

The term "crosslinker" refers to the chemical compound that binds one polymer chain to another one via covalent bonds or electrostatic interactions. The crosslinkers utilized in the present invention include, but are not limited to, trisodium trimetaphosphate (abbreviation "STMP"), sodium tripolyphosphate (abbreviation SUP), 1,4-butanediol diglycidyl ether (abbreviation "BDDE") and calcium ions. The term "crosslinking reaction" herein is used to describe the process of binding polymer chains to each other and is carried out in the presence of crosslinker or is realized via complex formation between two oppositely charged polymers. The non-limiting example of the crosslinking reaction between two oppositely charged polymers realized herein is the complex formation between sodium hyaluronate and chitosan acetate. The crosslinking reaction is carried out at room temperature or at higher temperatures, preferably but not limited to at 60° C. in pure water or in the presence of pH adjusting compounds (eg. hydroxides, acids, buffers) at acidic, neutral or basic pHs, preferably at pH above 3 and below 13.

In preferred embodiments, the crosslinking is preferably achieved by three different approaches: in the first approach the crosslinker, biopolymer and aqueous solution are mixed together in a way described below; in the second approach two oppositely charged polymers and aqueous solution are mixed together; and in the third approach the polymer is mixed with aqueous solution, moulded and the obtained semi-solid body is placed into concentrated solution of the crosslinker which is taken up and reacting.

Optionally, the semi-solid preparation can contain one or more biologically active materials or substances. The term "biologically active material or substance" includes but is not limited to cells for scaffold preparations, proteins, peptides, hormones, vitamins and other bioactive compounds, pharmaceutical drugs (for example, antibiotics, anesthetics, antipsychotics, antiseptics, etc). The biologically active substances can be added before or after crosslinking reaction.

Mixing of the components is the most important step in the present invention. The homogeneous mixture of the components is achieved, preferably, by grinding them together in a grinding mill or in a cryomill or by means of an extruder followed by kneading and moulding or directly by moulding under continuous pressure. For the better mixing of the components, it is preferred that extrusion can be used. All components in the grinding step can be solid or liquid or both, the temperature can be ambient or adjusted by addition of other components such as dry ice or liquid nitrogen. In the next step the obtained mixture can be kneaded at room temperature and moulded or directly pressed into a mould. The obtained composite (after kneading and/or during moulding) has a semi-solid consistency. The movement of the polymer chains and their rearrangement in the semi-solid state is limited, therefore the reasonable duration of the moulding is from several hours to few days depending on the crosslinking reaction and applied temperature. The moulded solid body is placed into excess water or buffer to swell and remove the unreacted materials and establish appropriate pH. After 1-3 days of swelling and/or washing the obtained hydrogel is weighted and dried (in an oven at temperatures below 200° C. or freeze-dried). The obtained solid bodies can be rehydrated. Besides, the solid body can be micronized and seeded in order to obtain microparticles of defined size, before rehydration.

Alternatively, the semi-solid composite after being moulded or/and micronized without a crosslinker and with or without biologically active substances, can be placed into an aqueous solution of a crosslinker for crosslinking reaction.

According to one preferred embodiment, a polymer or a plurality of polymers is/are provided as a powder and is/are mixed with crosslinker and an aqueous solution at water content below 70 weight %. The semi-solid, paste-like (modelling clay-like) mass is then moulded, optionally it can be micronized in order to obtain microparticles. The reaction can be carried out at ambient temperature as well as at increased temperature. The obtained solid body can be washed free from undesired components (ions, non-reacted crosslinker molecules, byproducts) in the excess amount of the aqueous solution.

FIG. 1 depicts one preferred method of producing a cross-linked biopolymer, comprising: providing a polymer or a plurality of polymers as a powder; mixing the polymer or the plurality of polymers with a crosslinker and an aqueous solution at a water content below 70 weight % to form a semi-solid, paste-like mass; and moulding the semi-solid, paste-like mass to obtain a solid body.

According to another preferred embodiment for producing a cross-linked biopolymer, a biopolymer is mixed with aqueous solution forming a semi-solid mass, optionally micronized. The crosslinking is realized by placing the kneaded mass (before or after drying) into a crosslinker solution. The crosslinked polymer matrix can be loaded with other biologically active substances, for example, proteins, peptides, vitamins, antioxidants, signaling molecules, antibiotics, conventional drugs etc. and/or cells.

Figure 2:
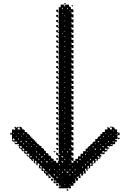
FIG. 2 depicts another representative method of producing a cross-linked biopolymer.

FIG. 2 depicts a method of producing a cross-linked biopolymer, comprising: mixing a biopolymer with an aqueous solution to form a semi-solid mass; and placing the mass into a crosslinker solution to form a crosslinked polymer matrix.

According to one preferred embodiment, loading of a polymer matrix with active ingredients is more preferable prior to carrying out a crosslinking reaction, especially in the case when the kneaded polymer mass is placed into a crosslinking solution.

According to yet another embodiment, namely when a crosslinker and one or more polymers are kneaded together, the later loading of a polymer matrix with active ingredients can be performed.

The crosslinking of hyaluronic acid and its derivatives can be achieved, for example, by means of reaction with divinylsulfone, by irradiation, phosphorous V containing reagents (trisodium trimethaphosphate) or with bifunctional or polyfunctional epoxides (1,4-butanediol diglycidyl ether). These crosslinking reactions are representative and non-limiting examples of the present invention.

A number of examples are presented below in order to illustrate the invention, without limiting the scope of the present invention in any way.

Example 1

5 g of sodium hyaluronate (MW 2 MDa) and 5 g of SMTP are weighed and mixed together in a grinding IKA Tube mill C S2000 with 25000 rotations per minute for 1 minute in intervals of 15 seconds with breaks of 1 second. The mixed powder was then hydrated with 10 ml of 0.2 M sodium hydroxide in the same mill by grinding for 30 seconds and kneading by folding and applying pressure until a homogeneous plastic mass is obtained. Five similar solid bodies were formed by pressing into a silicone mould, the sixth body was left in a form for 3 days under pressure at 60° C.

The sample 1 was left to dry at 60° C., the sample 2 was left in a closed vessel for equilibration at room temperature, the sample 3 was dried at ambient conditions, the sample 4 was moisturized in a steam machine for 30 minutes and dried at ambient conditions, the sample 5 was left for equilibration in a closed vessel at 60° C. After 3 days all samples were weighed and put into excess amount of phosphate buffered saline, pH 7.4. All samples were successfully crosslinked—since no increase of viscosity of the surrounding solution was observed, they remained in a separate phase keeping the form of the mould, however, increased in the size. The samples were swollen in a buffer until no increase of weight was detected. The equilibrium was achieved after ca. five days. The samples were weighed (the excess buffer is soaked away by means of a filter paper). The samples 1 and 3 remain turbid in appearance and less swollen than the other samples. The drying during crosslinking, however, leads to a partial degradation of the hyaluronic due to an increase of the sodium hydroxide concentration during the drying procedure. We assume, the degree of crosslinking can be adjusted by varying the water content, providing a higher degree of crosslinking at a lower content of water. The most homogeneous, smooth and transparent hydrogel is the one kept in the mould—it increased its weight by a factor of 10. The swelled hydrogels were dried at 60° C. and weighed. The obtained bodies are rigid, semi-transparent and deformed. All samples lost their weight compared to the initial dry weight that indicates that not all crosslinking molecules took part in the reaction and were removed in a swelling procedure. The samples 1-4 were rehydrated in a phosphate buffered saline and their shape and weight were recovered.

The crosslinking reaction was repeated at least three times, the results are consistent with the first trial. The temperature is important only in the first hours of the crosslinking reaction (results are not shown). It was observed that crosslinking under pressure in the moulds at 60° C. and at room temperature had no effect on the swelling behavior of the samples that indicates a similar crosslinking degree. Drying and re-swelling provide intact structures.

Example 2

In a second example, sodium hyaluronate was crosslinked by BDDE at low pH. First, 500 mg of acetic acid (Rotipuran 100%) was added to 1 g of 1,4-butanediol diglycidyl ether followed by addition of deionized water (Millipor) in the ratio of 1:6. The obtained solution is grinded with ca. 5 g of sodium hyaluronate (2 Mda) in IKA Tube mill C S2000 with 25000 rotations per minute for 1 minute in intervals of 15 seconds with breaks of 1 second. The mixture is then kneaded until homogeneous plastic mass is obtained. Seven solid bodies were formed by pressing of the mixture into silicone moulds and immediate removal of the bodies from the moulds. The eighth body was left in a form for 3 days under pressure at 60° C. before it was extracted. The sample 1 and 7 were dried at 60° C. for three days, 3 was dried at room temperature, samples 2 and 5 were left at room temperature in closed vessels, samples 4 and 6 were left in closed vessels at 60° C. After three days, the treated samples were placed into phosphate buffered saline, pH 7.4 (PBS) and left for swelling for at least three days. The samples swelled to a different extent and in most cases keep the form of the mould.

The crosslinking degree in these samples is higher than in samples crosslinked with STMP. All samples swelled in a lower extent (3 to 6-fold of the dry weight) and remain turbid (with exception of the sample moulded under continuous pressure for 3 days). Moreover, samples dried during crosslinking fall apart during swelling. The crosslinking degree is obviously dependent on the crosslinking concentration and, similar to the example 1, on aqueous content. Dry forms of samples remaining intact were observed. The swelled hydrogel crosslinked in a mould can be recovered without any problems after drying.

Example 3

Described herein is another example of a crosslinking reaction which is a complex formation between oppositely charged polyelectrolytes. Sodium hyaluronate bears negative charges at neutral pHs owing to carboxylic acid group in the D-glucuronic acid residue which are reacting with positively charged amino groups of chitosan acetate. Herein, 1 g of sodium hyaluronate is grinded with 1 g of chitosan acetate in IKA Tube mill C S2000 with 25000 rotations per minute for 1 minute in intervals of 15 seconds with breaks of 1 second followed by addition of 2 g of deionized water and further grinding for 30 seconds. A wetted mass is then kneaded and a sphere is formed, dried and is swollen in PBS. A swelling of hyaluronate chitosan complex is demonstrated in comparison with dissolution of pure chitosan acetate. The hydrogel of hyaluronate/chitosan is turbid and stable in aqueous solution (PBS) for more than one month. The water content in the complex is ca. 83%.

Examples 4 and 5

The other order of components addition is demonstrated in examples 4 and 5. In this case biopolymers are first kneaded with water, then placed into concentrated aqueous solution of multivalent counterions which are able to cross-link the charged groups in the biopolymer backbones.

In example 4, the chitosan acetate was first grinded with deionised water in the ratio of 1:1 and kneaded in a similar way as in the previous examples. Two spheres are formed: one is dried and the second one is crosslinked in 14 mg/ml aqueous solution of a crosslinker (sodium tripolyphosphate) for at least 20 hour and dried afterwards. The obtained dried crosslinked and non-treated chitosan samples are placed into phosphate buffered saline. The non-crosslinked chitosan slowly dissolves in buffer while the sample crosslinked in a sodium polyphosphate solution remain unchanged indicating the successful crosslinking.

The same crosslinking procedure was realized for sodium alginate kneaded with water in a ratio of 1:1. The semi-solid moulded sodium alginate was crosslinked overnight in 1 M calcium chloride aqueous solution. In order to prove the crosslinking success, the obtained solid body was placed into excess amount of deionized water and shape and size remained nearly unchanged.

Representative Methods of the Present Invention
  One Representative Method
    Biopolymer+Water - - - (knead, mold)→Semisolid body - - - (put into solution of a crosslinker)→Crosslinked semisolid body
  Another Representative Method (with Active Ingredient)
    Biopolymer+Active ingredient+Water - - - (knead, mold)→Loaded matrix - - - (put into solution of a crosslinker)→Crosslinked matrix loaded with an active ingredient
  Yet Another Representative Method
    Biopolymer (semidry)+Crosslinker (dry or semidry) - - - (knead, mold)→Matrix - - - (put into solution with or without active ingredient)→Swollen hydrogel without or with an active ingredient
  Still Another Representative Method
    Biopolymer (dry)+Crosslinker (dry or semidry)+Active ingredient - - - (knead, mold)→Crosslinked matrix with active ingredient

The invention claimed is:

1. A method of producing a cross-linked biopolymer, comprising:
   providing a polymer or a plurality of polymers as a powder;
   mixing the polymer or the plurality of polymers with a crosslinker and an aqueous solution at a water content below 70 weight % to form a homogenous semi-solid, paste-like mass;
   moulding the semi-solid, paste-like mass; and
   performing a cross-linking reaction to obtain a solid body.

2. The method of claim 1, further comprising micronizing the solid body to obtain microparticles.

3. The method of claim 1, further comprising washing the solid body.

4. The method of claim 1, wherein the mixing is carried out at ambient temperature.

5. The method of claim 1, wherein the cross-linking reaction is carried out at higher temperatures compared to ambient temperature.

6. The method of claim 1, wherein the mixing is carried out at lower temperatures compared to ambient temperature.

7. The method of claim 1, further comprising adding one or more active ingredients before the crosslinking reaction.

8. A method of producing a cross-linked biopolymer, comprising:
   mixing a biopolymer with an aqueous solution at a water content below 70 weight % to form a semi-solid mass;
   placing the semi-solid mass into a crosslinker solution; and
   performing a crosslinking reaction to form a crosslinked biopolymer matrix.

9. The method of claim 8, further comprising adding one or more active ingredients before performing the crosslinking reaction.

10. The method of claim 8, wherein the biopolymer comprises hyaluronic acid.

11. The method of claim 1, comprising mixing the polymer or the plurality of polymers with a crosslinker to form a mixed powder, and then hydrating the mixed powder with the aqueous solution.

12. The method of claim 1, wherein at least one of the polymers or the plurality of polymers is hyaluronic acid.

13. The method of claim 1, wherein moulding comprises pressing the semi-solid, paste-like mass into a mould, and crosslinking is performed under continuous pressure.

14. The method of claim 1, wherein mixing comprises grinding in a grinding mill.

15. The method of claim 14, wherein mixing further comprises using an extruder.

16. The method of claim 1, comprising mixing the polymer or the plurality of polymers with a crosslinker and an aqueous solution at a water content of 50 weight % or lower.

* * * * *